United States Patent
Selner

(10) Patent No.: US 8,490,301 B2
(45) Date of Patent: Jul. 23, 2013

(54) ADJUSTABLE FOREFOOT POSTING FOR ORTHOTIC

(76) Inventor: Allen Joseph Selner, Manhattan Beach, CA (US)

(*) Notice: Subject to any disclaimer, the term of this patent is extended or adjusted under 35 U.S.C. 154(b) by 0 days.

(21) Appl. No.: 13/326,318

(22) Filed: Dec. 14, 2011

(65) Prior Publication Data

US 2012/0151803 A1 Jun. 21, 2012

Related U.S. Application Data

(60) Provisional application No. 61/425,196, filed on Dec. 20, 2010.

(51) Int. Cl.
*A43B 7/24* (2006.01)

(52) U.S. Cl.
USPC .................... 36/100; 36/142; 36/144

(58) Field of Classification Search
USPC ............... 36/15, 42–44, 100, 101, 142–144, 36/150–160
See application file for complete search history.

(56) References Cited

U.S. PATENT DOCUMENTS

| | | | | |
|---|---|---|---|---|
| 5,036,604 | A * | 8/1991 | Rosen | 36/88 |
| 5,345,701 | A * | 9/1994 | Smith | 36/144 |
| 5,685,092 | A | 11/1997 | Prieskorn | |
| 5,768,803 | A | 6/1998 | Levy | |
| 6,098,319 | A * | 8/2000 | Epstein | 36/159 |
| 6,125,557 | A | 10/2000 | Brown | |
| 6,269,554 | B1 * | 8/2001 | Silvestrini et al. | 36/144 |
| 6,609,314 | B1 | 8/2003 | Dubner | |
| 6,662,475 | B2 * | 12/2003 | Lewia | 36/130 |
| 6,804,902 | B1 | 10/2004 | McCracken et al. | |
| 7,272,900 | B1 * | 9/2007 | Epstein | 36/159 |
| 7,681,333 | B2 | 3/2010 | Dardinski et al. | |
| 2003/0159314 | A1 * | 8/2003 | Lewia | 36/130 |
| 2006/0059726 | A1 * | 3/2006 | Song et al. | 36/142 |
| 2008/0060229 | A1 | 3/2008 | Epstein | |
| 2008/0289219 | A1 | 11/2008 | Nakano | |

FOREIGN PATENT DOCUMENTS

| | | |
|---|---|---|
| CA | 2245218 | 12/1999 |
| JP | 2000125903 | 5/2000 |
| KR | 200265394 | 2/2002 |
| WO | WO2006050092 | 5/2006 |
| WO | WO2008153266 | 12/2008 |
| WO | WO2009156758 | 12/2009 |

OTHER PUBLICATIONS

PCT/US2011/065078 International Search Report, Jul. 25, 2012, Kipo Allen Joseph Selner.
PCT/US2011/065078 Written Opinion of the International Searching Authority, Jul. 25, 2012, Kipo Allen Joseph Selner.

* cited by examiner

*Primary Examiner* — Marie Patterson
(74) *Attorney, Agent, or Firm* — George P. White

(57) ABSTRACT

An orthotic device has a readily adjustable variable forefoot posting system. In some embodiments, a generally planar plate is pivotally coupled to a foot-receiving shell. The plate is generally under the arch and not in contact with the supporting surface when in a neutral position. Along the plate's perimeter are raised regions that can be deployed into position as a forefoot post via pivoting the plate. In some versions, adjustability is via a sliding motion. Some areas have a greater height than others do and these raised areas or protrusions can be set at either an inner side or an outer side. Depending upon the shape of the ridges on the plate and the plate's pivoted position, a range of tilts can be variability provided. The plates can be part of an interchangeable system providing more options. Professional versions can have a greater range of settings than consumer versions.

27 Claims, 11 Drawing Sheets

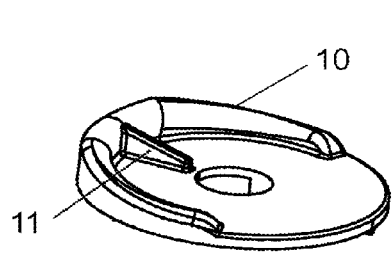
FIG. 5A
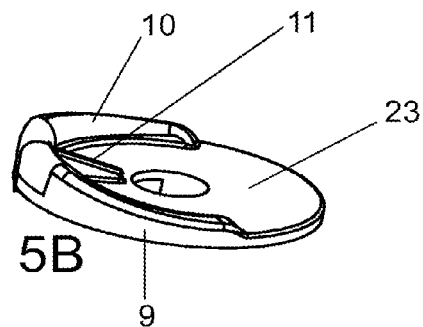
FIG. 5B
FIG. 6
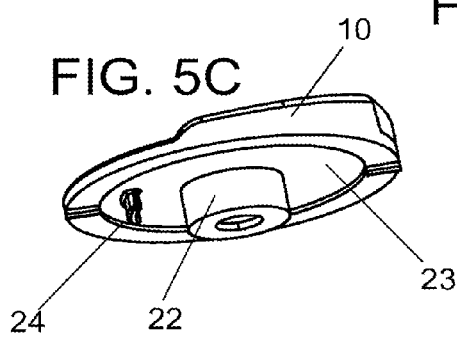
FIG. 5C
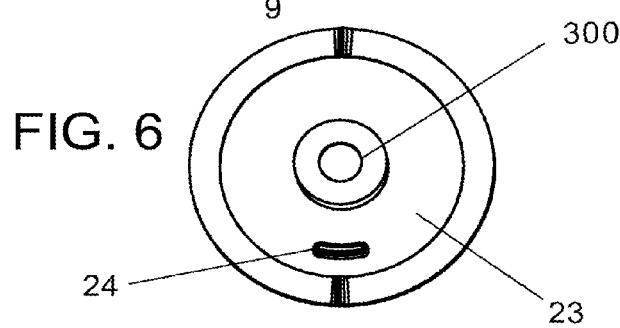
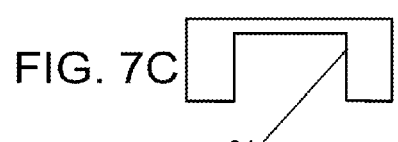
FIG. 7C
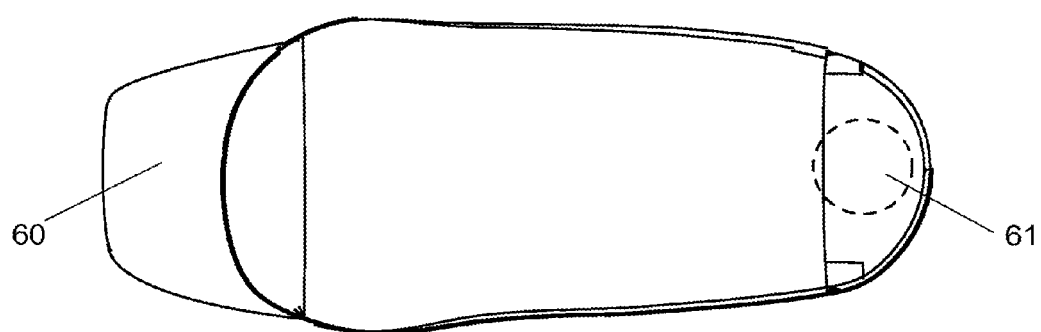
FIG. 7A
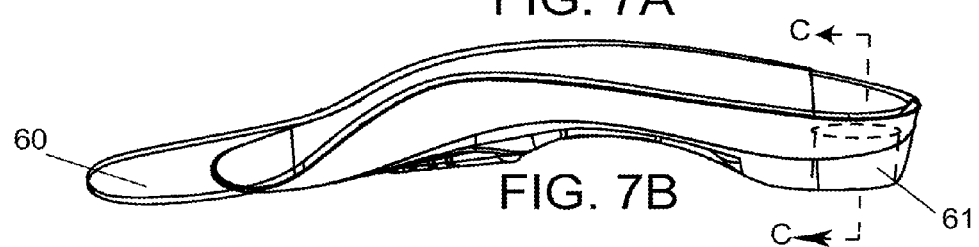
FIG. 7B

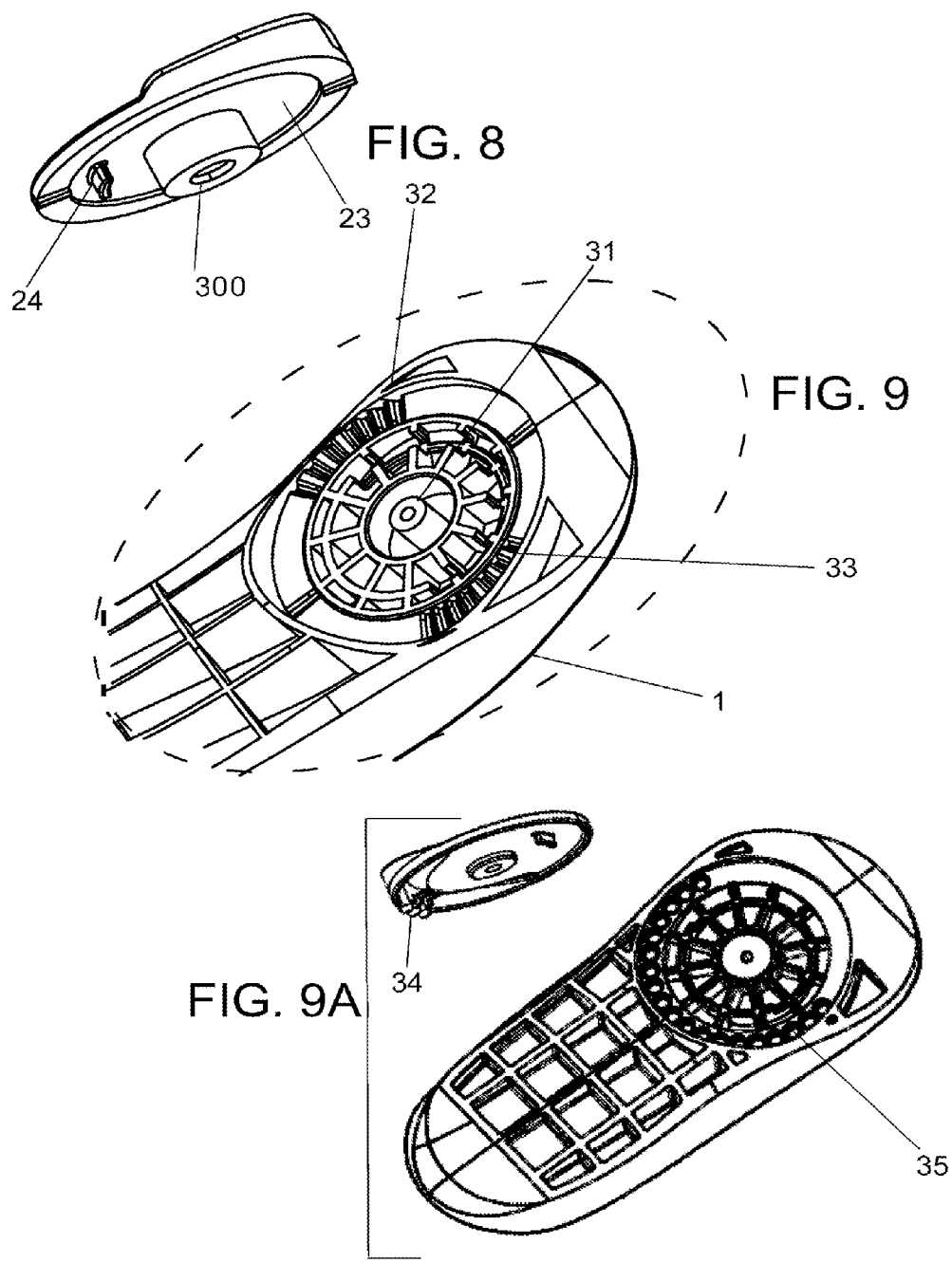

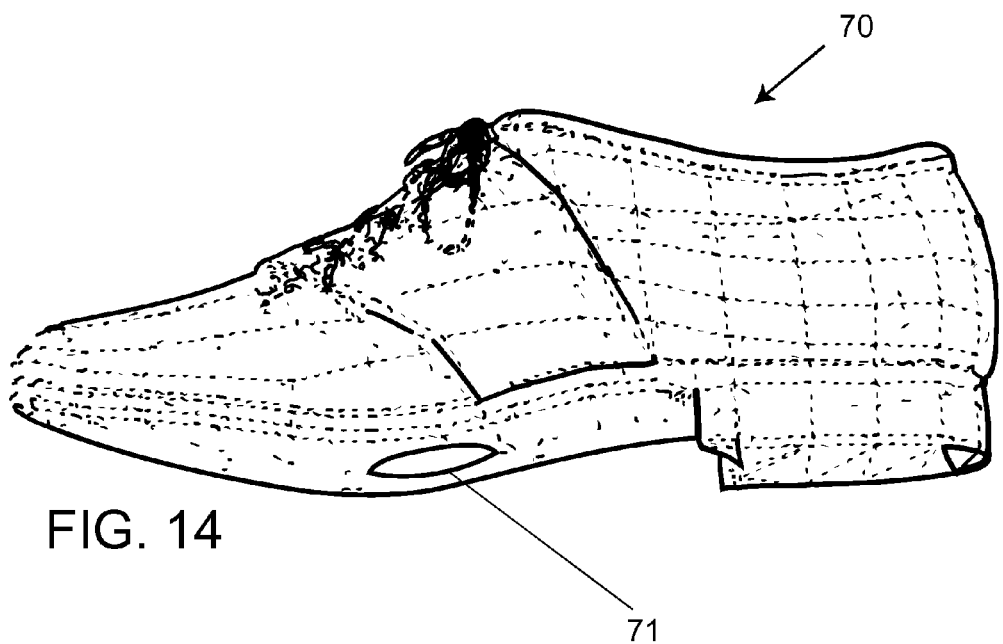
FIG. 14
FIG. 15A
FIG. 15B
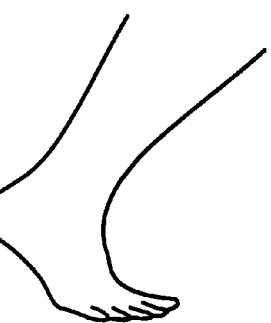
FIG. 15C

ADJUSTABLE FOREFOOT POSTING FOR ORTHOTIC

RELATED APPLICATIONS

This application claims the benefit of U.S. provisional patent application 61/425,196 filed Dec. 20, 2010, under 35 U.S.C. 119 (e) and is hereby incorporated herein by reference in its entirety.

FIELD

The present teachings relate generally to appliances that are inserted into or associated with footwear to provide foot support to improve alignment of the lower extremities. More specifically, it relates to devices and methods for adjustable forefoot posting.

BACKGROUND

Since feet are the foundation on which the rest of the body is supported, foot misalignment can cause many forms of discomfort and disorders. The ligaments and muscles connect the various bones and joints. When weight bearing, the foot, leg, and hip form a closed kinetic chain. Changes in one area will affect all the other areas. This means that a small difference in alignment of foot position or foot motion can have significant effect on the rest of the lower body. So-called functional orthotics can be used to realign the foot relative to the supporting surface and the foot relative to the rest of the body during a gait. These devices are called upon to solve difficult problems in a complex area of anatomy, physiology, and biomechanics.

Functional orthotics are devices usually made by a podiatrist. They often involve a forefoot post that is a raised area on the underside of the orthotic. A problem however, is that there is no exact methodology of being confident that the foot is aligned to provide the desired clinical benefit. Proper posting prevents excessive motion as a compensation for structural problems in the foot. Functional orthotics with podiatrist prescribed posts have the problem that they are fixed and can only be changed by the doctor grinding off or gluing on material. Since the foot in motion is such a complicated system, prescribing and devising these functional orthotics is not yet an exact science and can require multiple visits to get to the point of providing relief for a patient. If a patient has specialized needs for particular activities such as running or golfing, that could require a second, differently shaped orthotic with its own set of multiple visits in order to be produced correctly.

With a mass produced orthotic there are generally no posts at all because there are so many different foot types that one set of fixed posts could not possibly work on the myriad of foot types. Furthermore, many orthotics are made of relatively soft materials that, while better tolerated, have very limited capabilities of resisting ground reactive forces and thus have limited ability to realign foot positions during the execution of a gait.

SUMMARY

Devices according to the teachings herein can solve the problem of repeated visits and adjustments of a forefoot post by an adjustable posting system for an orthotic for the foot. A repositionable selector can be located on the underside of a foot-supporting platform, possibly under the medial arch region. The slot can have locations of various heights that can be positioned to either the inner side or the outer side of the foot-receiving platform. Depending on the height of the particular structure that is positioned to act as a post, a specific degree of tilt and direction will be obtained. Encompassed within these teachings is fine tuning of the posting by the wearer as they engage in their daily activities to achieve a level of comfort that may not be reached by repeated visits to have a traditional orthotic modified.

BRIEF DESCRIPTION OF THE DRAWINGS

FIG. 1A shows the first example orthotic in a plan view;

FIG. 1B shows the device of FIG. 1A in perspective from the side at a 45-degree angle;

FIG. 1C shows the device of FIG. 1A in perspective from the side at a 90-degree angle;

FIG. 1D shows the device of FIG. 1A in perspective from the side at a 135-degree angle;

FIG. 1E shows the first example orthotic from the bottom;

FIGS. 5A-5C show various perspective views of the lift plate to illustrate its various features;

FIG. 6 is a plan view of the bottom of the lift plate;

FIGS. 7A-7C are a plan view, a side view and a rear sectional view along C-C of an variation of the first embodiment; this embodiment has a flexible front extension and has a hollow region in the heel to provide for added springiness;

FIG. 8 shows an enlarged view lift plate of the initial embodiment;

FIG. 9 shows an enlarged view of the region of the bottom surface of the body that accommodates the lift plate;

FIG. 9A shows an alternate design for the interface between the upper surface of a lift plate and the lower surface of a foot receiving body;

FIG. 11A shows a perspective view from the bottom with the selector exploded;

FIG. 12A shows a perspective view from the bottom showing the left and right selectors exploded;

FIG. 13A shows a perspective view from the bottom with the selector exploded;

FIG. 13B shows a bottom view with the selector turned to the right providing a right forefoot post;

FIG. 13C shows a bottom view with the selector turned to the left providing a left forefoot post;

FIG. 13D shows a bottom view with the selector in the center and retracted;

FIG. 14 is a perspective view of an embodiment built into a shoe;

FIGS. 15A, 15B, and FIG. 15C are illustrations of three different phases of a human gait cycle;

DETAILED DESCRIPTION

Figure 1:
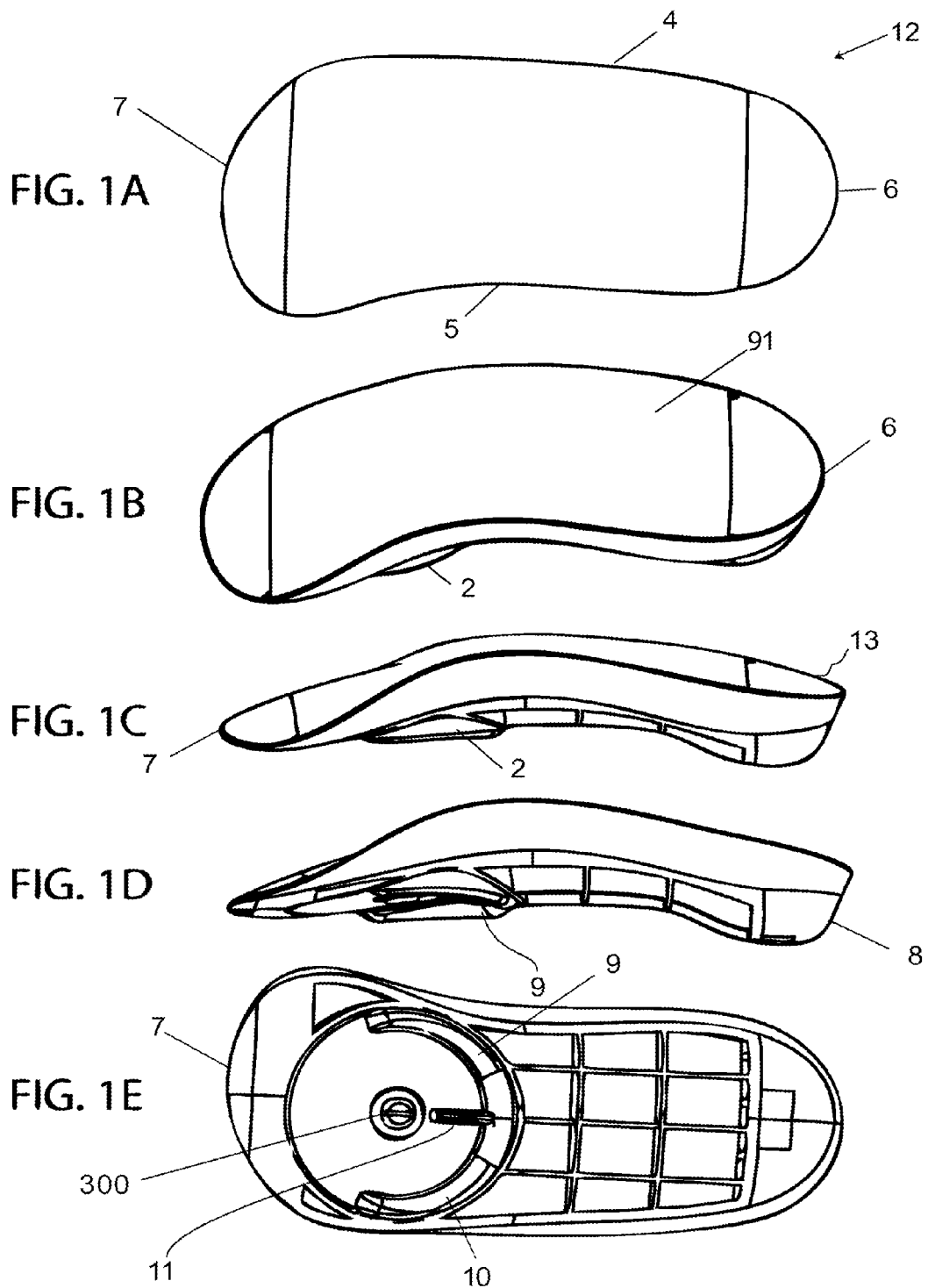
FIGS. 1A-1E show a right foot orthotic of a first embodiment from various angles.

In conjunction with the included drawings this detailed description is intended to impart an understanding of the teachings herein and not to define their metes and bounds.

Understanding of the Problem

A gait cycle consists of heal contact, mid-stance, propulsion (weight bearing), and the swing phase, prior to heal contact again. During the early phase of a gait cycle the foot must be flexible to accommodate uncertainty in the surface being walked upon and to absorb the shock of the foot hitting the supporting surface. Later in the gait the foot must be rigid in order to provide the propulsive strength needed in the push-off. The foot has the capability to lock and unlock primarily due to the structure of the subtalar joint, a joint that is directly below the ankle. One motion called pronation (or flattening) occurs at the subtalar joint and allows unlocking of the bones of the foot. An opposite motion, called supination (raising of the arch) occurs at the subtalar joint and results in locking of the bones of the foot.

The goal of a functional orthotic is to not merely raise or lower the arch as has been commonly assumed but to redirect forces, decelerate motion and redistribute pressure in such a manner resulting in an optimal gait pattern for the particular foot type and task. The weight-bearing part of the gait cycle is from heel contact to toe off and is controlled by the ground reactive forces in response to the foot hitting the ground. An orthotic can alter the gait cycle by redirecting forces, decelerating motion, and redistribution of pressure. When the foot is properly aligned in this optimal position the excessive forces generated by the previous malalignment syndrome are reduced significantly. This most optimal gait pattern results in a better-aligned subtalar joint, locked forefoot or midtarsal joint, reduced excessive forces and decreased stress on the muscles of the lower extremity and improved balance and proprioception. These changes have been demonstrated to lead to improved clinical outcomes by decreasing pain and improving function. Thus, the doctor's goal in making custom-made devices should be to place the foot in the optimal position. Since small changes may results in large improvements in the clinical outcomes for patients, the best device would permit the patient to find the most optimal gain pattern at the lowest cost. FIGS. 15A, 15B and 15C show the heel contact, mid-stance and propulsion phases of a gait cycle.

Since the initially described, adjustable orthotic has seven different positions it can create seven different gait patterns, one for each setting. The question arises as to which particular gait pattern is the best clinically for a given foot and lower extremity of a particular individual. There is a clinical understanding that there is a most optimal gait pattern in which the excessive forces are properly controlled, the muscle firing sequences work best and the proprioceptive and balance mechanisms work best. The adjustable orthotic allows both the clinician and patient to seek out the most optimal control. Since very small changes in the orthotic can create significant clinical outcomes for the patient these changes can demonstrate profound improvement in clinical outcomes for foot, leg, knee, and back pain.

Introduction

The embodiments presented herein include a rigid or semi-rigid orthotic plate that reaches from the heel up to the metatarsal heads. These embodiments also include a forefoot post that is a feature of a repositionable lift plate. Generally, other than the area acting as a post, the rest of the lift plate is low enough to be out of the way of surface-support. Deploying of regions of predetermined heights to either the inner or outer forefoot posting position provides an adjustable, functional orthotic forefoot posting system capable of tilting the orthotic in either a rolling-in or rolling-out direction. A goal and method of orthotic prescription involves the clinician determining a foot position that results in desired clinical benefits. Often to find an optimal position has been the repeated trials mentioned above. Adjustability can provide a tune-ability to the wearer's perception of comfort and can provide for real-time changes to respond to different footwear and different activities.

Teaching Related to the Problem

The benefits and use of forefoot posting and its comparison to rearfoot posting are well known to those skilled in the art. Those skilled in the art also are aware of the importance of feet and gait as the foundation of the rest of the body. Herein incorporated by reference in their entirety are U.S. Pat. No. 4,702,255, Schenki, U.S. Pat. No. 5,345,701, Leland Smith, and U.S. patent application 2009/0183389, Miller.

Structure

As seen in FIGS. 1A-1E a right foot orthotic 12 is shown from various angles. It has an arcuate body 1 with a circular lift plate, or tilt selector 2 attached to the body by a screw 3. The lift plate is generally planar with two raised ridges: an inner ridge 9, and an outer ridge 10. In FIG. 1A the orthotic is seen from the top.

In this plane it has a concave shape from the outer edge 4 to the inner edge 5 and are to accommodate a heel 13 (seen in FIG. 1C) at its opposing back edge 6.

As seen in FIG. 1B, this top surface 91 is generally shaped to receive a wearer's foot and may be produced in a variety of sizes. The orthotic has a front edge 7 and an opposing back edge 6 at the heel 13.

From the side, as seen in FIG. 1C, the orthotic body is convex in its major dimension, providing for a raised arch in its central region. In this view and others, a ridge 9 of the lift plate 2 is visible. The bottom surface of the foot orthotic is seen in FIGS. 1D and 1E. In the specific pictured device of FIGS. 1D and 1E the selector's coupling to the body is such that it is pivotable about its center. In this case, a screw 3 establishes the pivot point. Other fasteners such as rivets might used instead of a screw. A user manipulates the orientation of the lift plate via grasping the selector handle 11 and providing a turning or twisting force. In all of these mentioned figures, the lift plate is in a neutral position.

Figure 2:
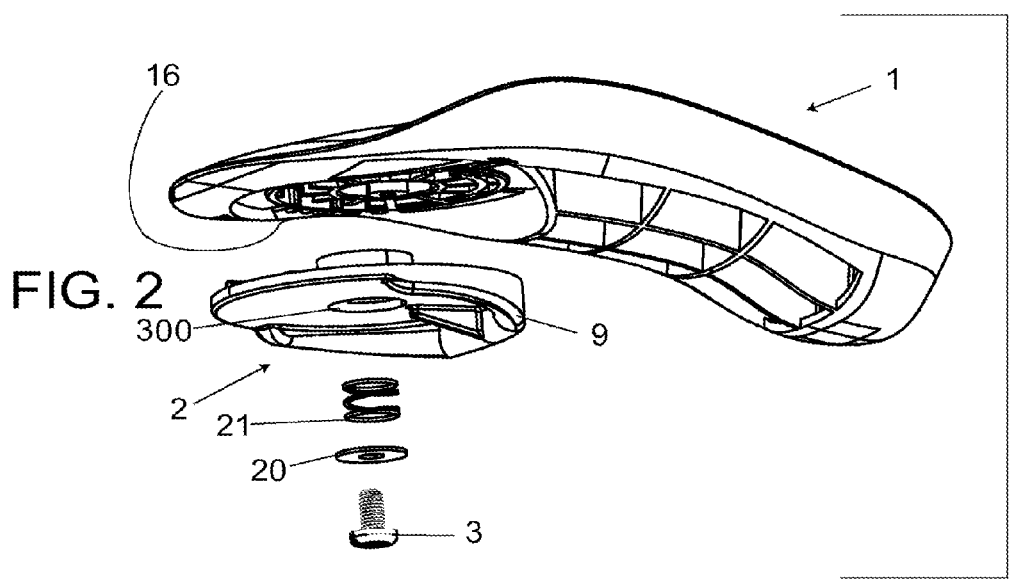
FIG. 2 shows an exploded version of the embodiment of FIG. 1A.

FIG. 2 shows an exploded version of this embodiment illustrating the body 1, the lift plate 2, a screw 3, a washer 20, and a spring 21. This figure also illustrates the position of the lift plate on the underside of the body and shows the lift plate in its neutral position wherein no part of the lift plate touches the "supporting surface". By the supporting surface, it is meant the flat plane upon which the orthotic is resting. In use, it would be in a shoe or other footwear that, in turn, would be touching the supporting surface.

Figure 3:
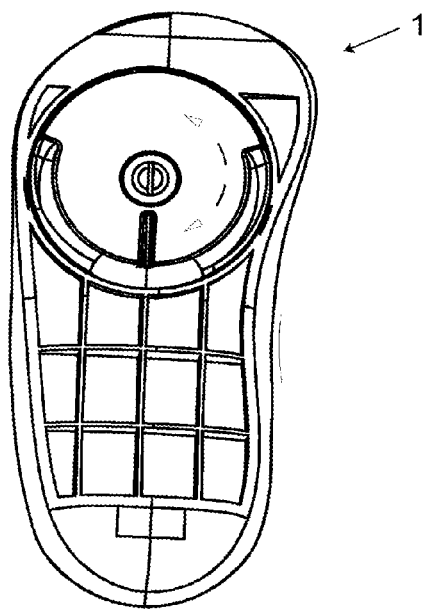
FIG. 3 shows the bottom surface of the orthotic body of FIG. 1A with the lift plate removed.
Figure 4:
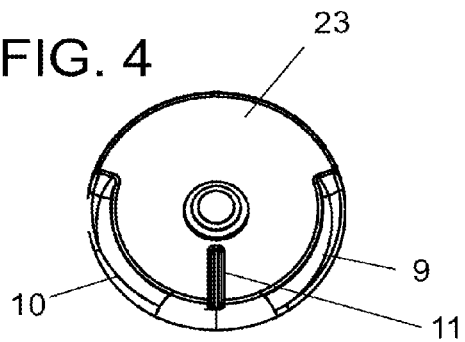
FIG. 4 shows a plan view of the lift plate in isolation.

FIG. 3 shows the bottom surface of the orthotic body 1 with the lift plate removed and FIG. 4 shows a plan view of the lift plate 2 in isolation. The region of the lower surface of the body for accommodating the lift plate 16 has a circular shape generally complementary to the lower surface of the lift plate 2.

FIGS. 5A-5C show perspective views of the lift plate illustrating its various features. FIGS. 5A and 5B show the inner and outer ridges and depict that in the pictured version the ridges are "piecewise flat". That is, each ridge is made up of a small number of discontinuous flat ramped areas, each of a different height and slope. FIG. 5C allows the bottom surface 23 of the lift plate to be seen. It is generally planar with a central shaft 22 that mates with a corresponding circular opening in the body when assembled.

A detent tab 24 offset between the center of the lift plate and its circumference extends downward, normal to the plane of the bottom of the lift plate. This feature is also seen in FIG. 6, a plan view of the bottom of the lift plate.

FIGS. 7A, 7B and 7C show views of a variation on this embodiment. This version has a flexible extension 60 at the front end of the rigid foot-receiving platform. In the side view of FIG. 7B the deeper heel and greater curvature of the platform can be seen. This version is depicted with a hollow cylindrical area 61 under the heel region. By leaving a relatively thin circular "drum head" of material above the hollow area a degree of "trampoline" springiness is added. This hollow region can be effective with about 0.125 inches of material above it. This optional hollow region might be shapes other than cylindrical.

FIGS. 8 and 9 respectively show an enlarged view of the lift plate of the initial embodiment and an enlarged view of the region of the bottom surface of the body that accommodates the lift plate. The center of that region has the lift plate mounting hole 31 that the screw goes into to secure the lift plate. In order to resist unintended pivoting, the detent tab 24 of the lift plate can abut either an inner 33 or outer 32 region of waves of curved features of the body. The increased force needed to pivot the lift plate prevents inadvertent turning during use. Other detent structures include a ball 34 and socket 35 seen in FIG. 9A. They can be designed according to a trade-off in strength of retention of a set position and degree of difficulty in changing positions.

When at an extreme tilt angle at some point in a gait cycle the rear-most portion of the orthotic plate might tilt to such a degree that either the left or right side might come off the ground. To enhance stability in these cases, both the left most and right most rear corners of the orthotic plate can have a small flat region that is at such an angle as to be parallel to the ground when the opposite side comes off the ground.

Operation

First Embodiment

Figure 10A:
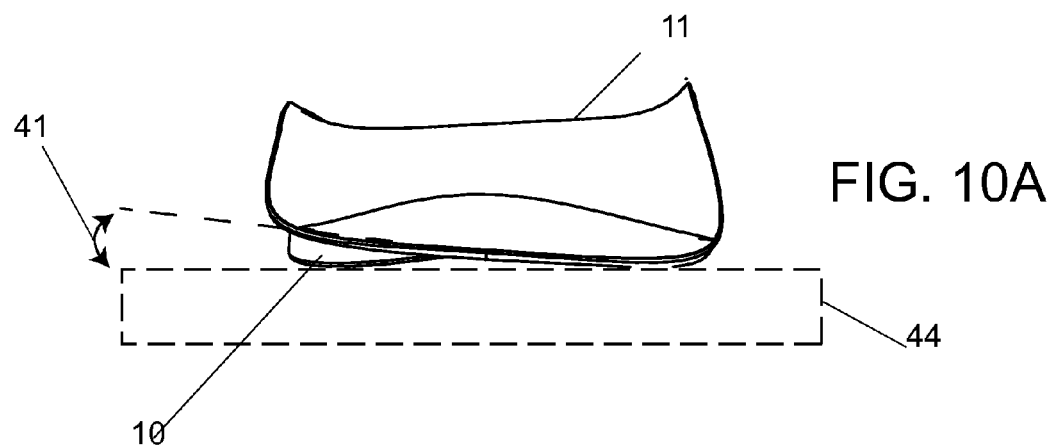
FIG. 10A shows a front view of the device of FIG. 1A with the lift plate in an outer posting position.
Figure 10B:
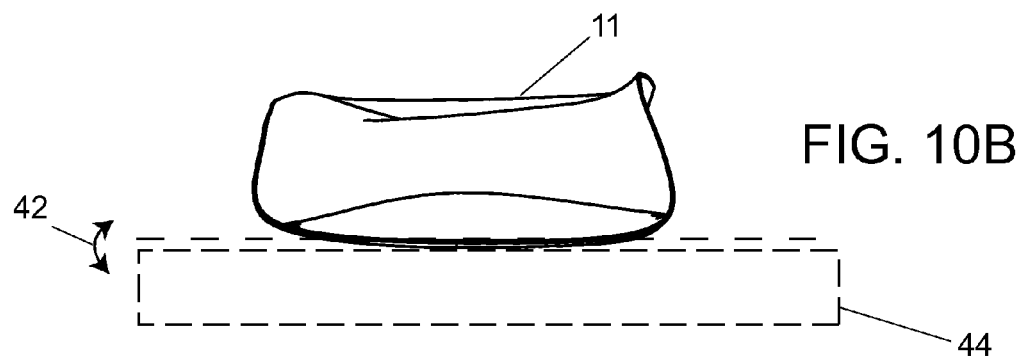
FIG. 10B shows a front view of the device of FIG. 1A with the lift plate in its neutral position.
Figure 10C:
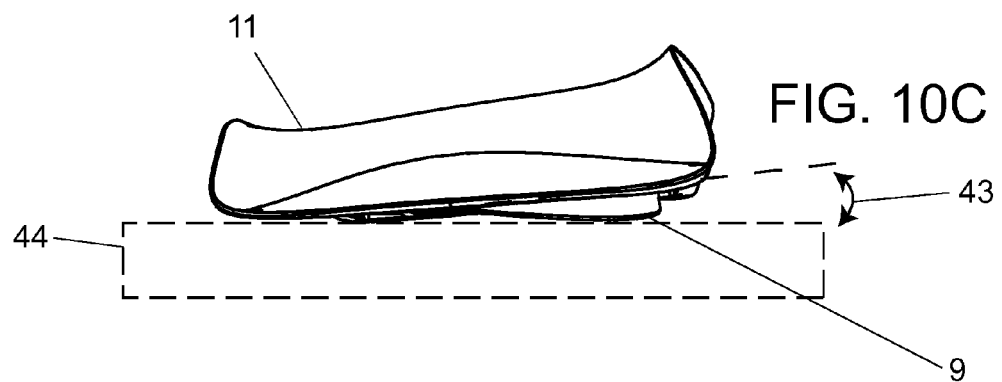
FIG. 10C shows a front view of the device of FIG. 1A with the lift plate in an inner posting position.

The first embodiment described and illustrated above is an orthotic device worn in a shoe or other footwear. To operate this embodiment, the tilt selector handle is used to pivot the lift plate to place a portion of its raised perimeter at a location that allows the raised portion to act as a forefoot post. The result of the operation is shown in FIGS. 10A-10C. In FIG. 10B the lift plate is in its neutral position and therefore no portion of it is touching the supporting surface or visible from this front view. In contrast FIG. 10A shows the lift plate pivoted as to create a forefoot post on the outside, tilting the forefoot to the inside by a specific angle 41. FIG. 10C shows the opposite state. The lift plate is turned to place a raised area at the inner forefoot post area, tilting the foot to the outside. The supporting surface reference 44 and the respective tilt angles 41 42 43 illustrate the phenomena.

Figure 10D:
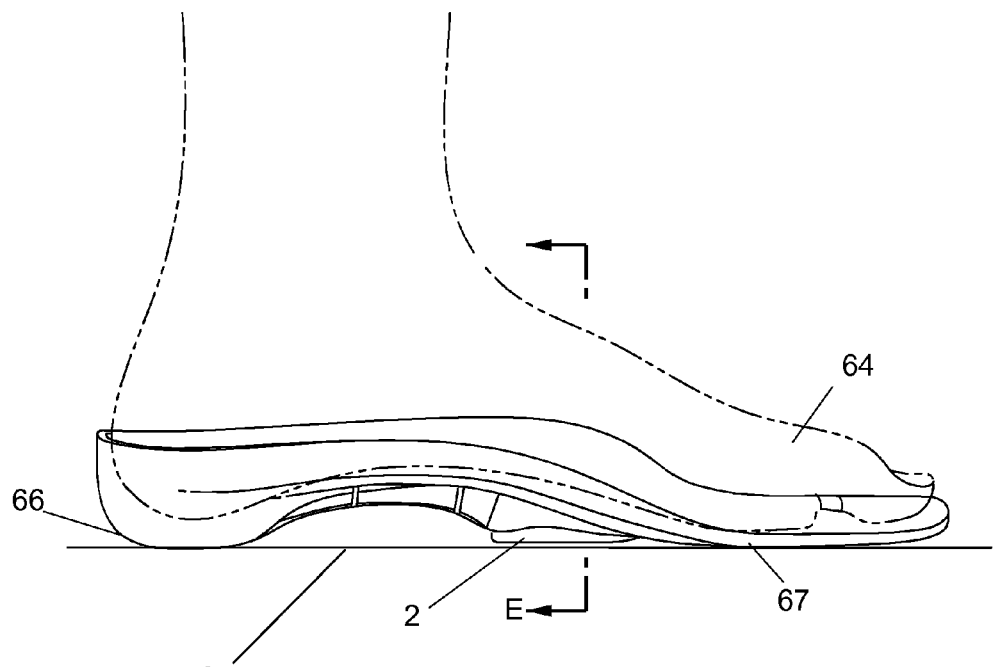
FIG. 10D is a side view of the device of FIG. 1A in a neutral position with a foot resting on the orthotic plate.
Figure 10E:
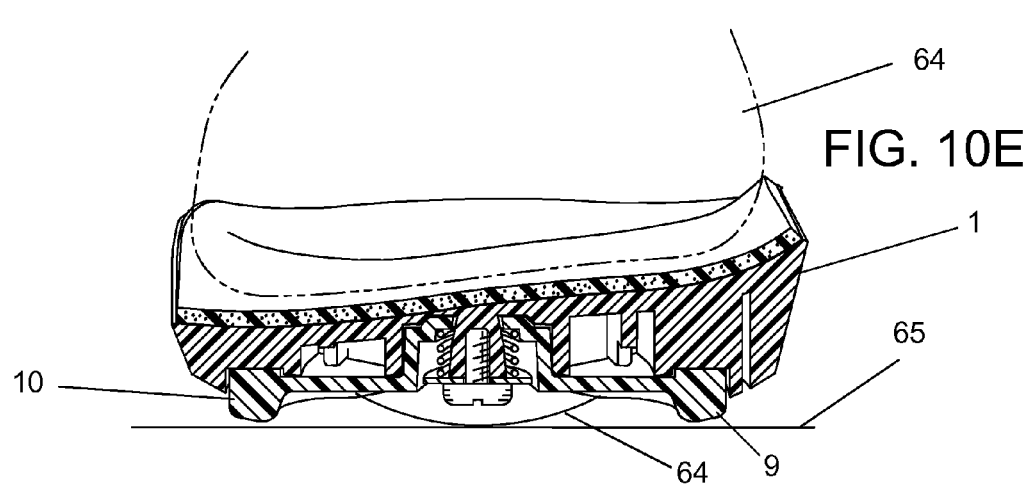
FIG. 10E is a sectional view taken along E-E of FIG. 10D.

FIGS. 10D and 10E illustrate the neutral case of 10B in other views. A foot 64 is shown resting on this first orthotic embodiment set to the neutral position and resting on a supporting surface 65. Although the raised portion of the selector is close to the supporting surface, they are not touching. The orthotic is supported at its heel 66 and metatarsal positions 67. FIG. 10E is a sectional view of the foot and orthotic in FIG. 10D along the line E-E.

Of course, the possible tilting is not restricted to planes representing a pure inversion or eversion. In general, the posting will support the foot in a more complex plane. In many versions, there will be indicia for example, 1P, 2P 3P N 3S, 2S, and 1S, along the circumference of the body region that accommodates the lift plate. The indicia can be used, possibly with accompanying instructions, to set the tilt to either deal with a valgus or a varus biomechanical issue of the wearer's condition. For a unit marketed to consumers, the range of tilt might be limited to 4 degrees. A unit for professional use might provide for a greater tilt, up to 8 degrees for example. This arrangement would prevent a consumer from a setting that might be extreme and unhealthful for them. With the professional unit, a podiatrist could treat a wider range of issues.

Since the weight of the body shifts to various parts of the foot during a gait, the position of a post can determine the gait phase in which the post is "active". One way to say this is, the shape and configuration of a pivot position of the lift plate can determine both an angle and the point in the gait cycle that the angle comes into play.

It has been said that many people could be helped by nothing more sophisticated than stuffing a sock in their shoe. On the other hand, podiatrists often have a patient that goes from pain to joy after only a very small change in an orthotic. In many cases, those fine adjustments could generally not have been made in any manner other than by seeing how it felt to the wearer. An embodiment with a continuous ridge, or one with a set of interchangeable lift plates having a wide range of properties can allow a person to "try on" a functional orthotic with a range of angles and subtle differences. With a current custom orthotic, this requires grinding away material, adding material, and is imprecise and not reliably repeatable.

As an off-the shelf device available in a variety of sizes and types, embodiments could provide a good deal of the benefit otherwise only available with a podiatrist's custom orthotic. Systems can be deployed to help consumers make measurements and recommend versions of embodiments and settings. Another use of an adjustable forefoot posting system can be for individuals who partake in particular sports. A golfer might set her lift plates differently in the left and right feet in order to have the unique support that is optimal for each foot during a swing. In addition some embodiments can feature interchangeable selectors. In versions where interchangeable selectors are provided for a user might switch selectors for differing activities or to accommodate different footwear. Skiing is one example that would benefit from this option.

Adjustability can also be a benefit for young patients that might slowly grow out of a problem and can have the tilt readjusted over time. Some other patients might require such a large correction that it needs to be "dialed up" gradually.

Second Embodiment

Figure 11A:
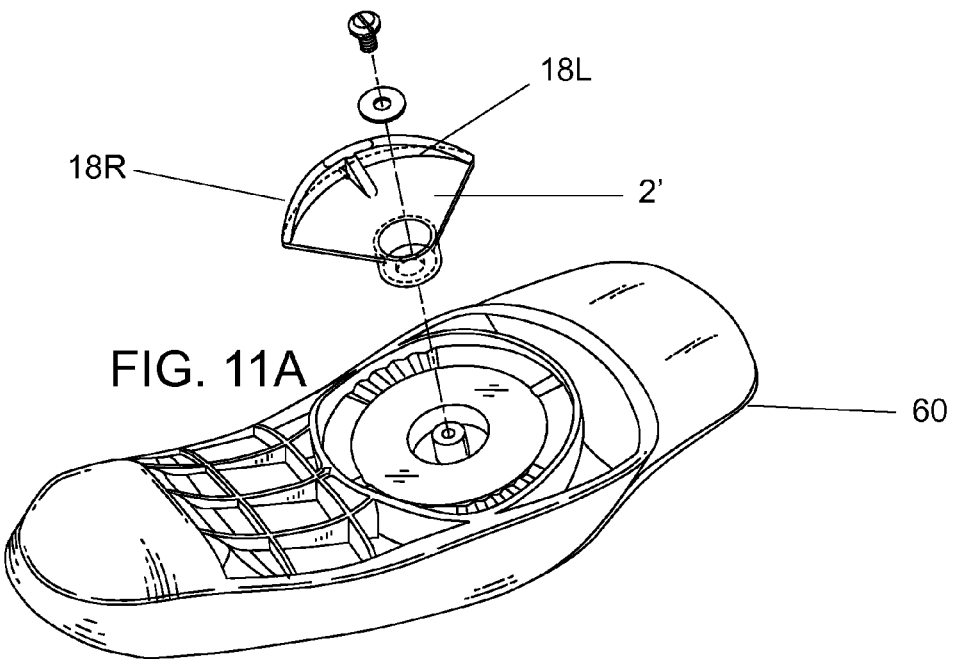
FIGS. 11A, B and C are views of the second embodiment.
Figures 11B, 11C:
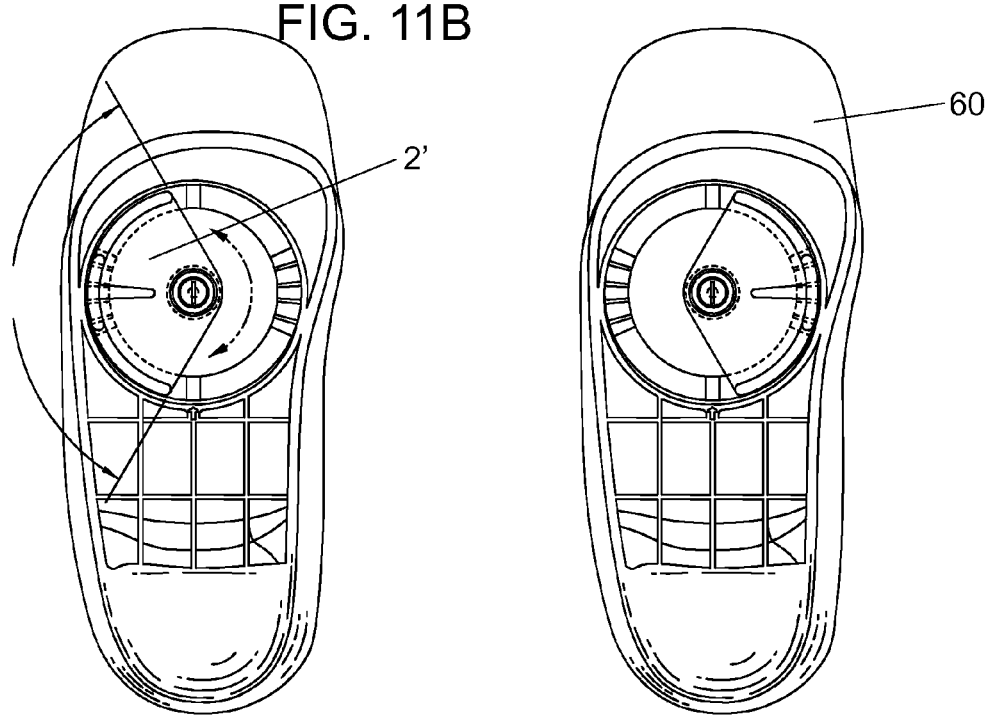
FIG. 11B shows a bottom view with the selector turned to the right providing a right forefoot post.
FIG. 11C shows a bottom view with the selector turned to the left providing a left forefoot post.

FIGS. 11A-11C show a second embodiment. In this embodiment the lift plate 2' is a "slice of pie" of a circle. The perimeter has two symmetric beveled ramps 18R 18L. FIGS. 11B and 11C are both bottom views showing the slice of pie. FIG. 11B shows the position of the lift plate 2' tilting the orthotic up at the right while FIG. 11C shows the position of the lift plate 2' tilting the orthotic up to the left.

Third Embodiment

Figure 12A:
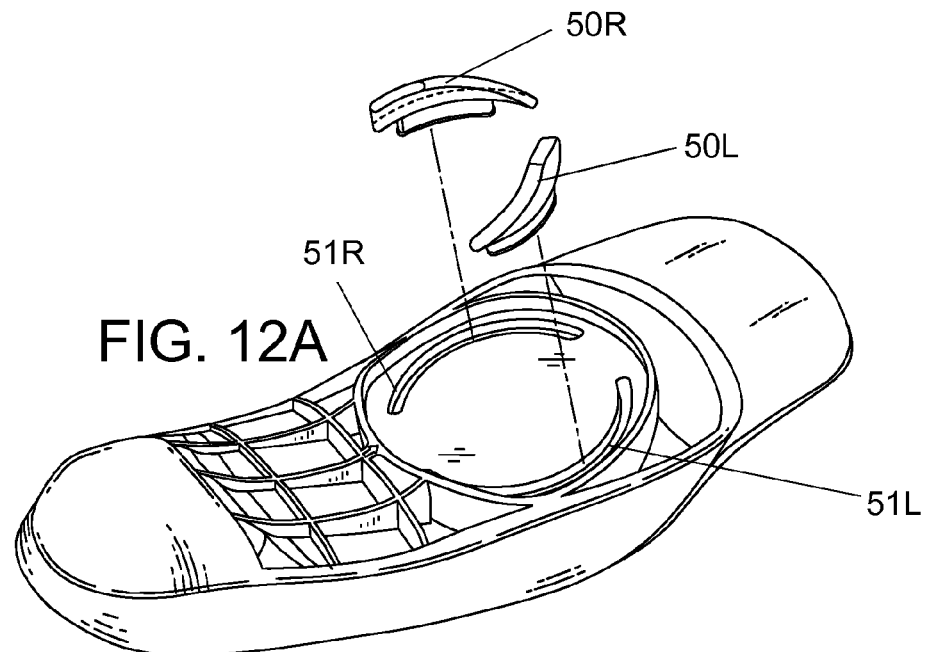
FIGS. 12A, B and C are views of the third embodiment having slidable posting.
Figures 12B, 12C:
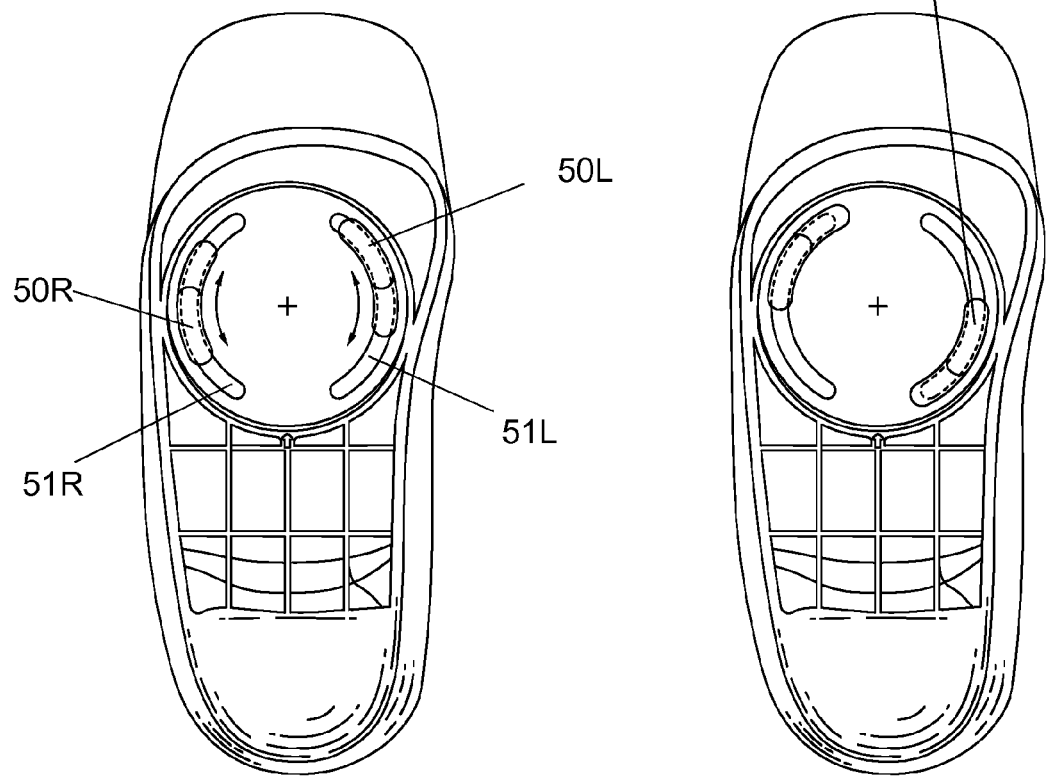
FIG. 12B is a bottom view showing the slidable movement.
FIG. 12C is a bottom view showing the right selector advanced to posting position while the left selector is retracted and out of the way.
Figure 13A:
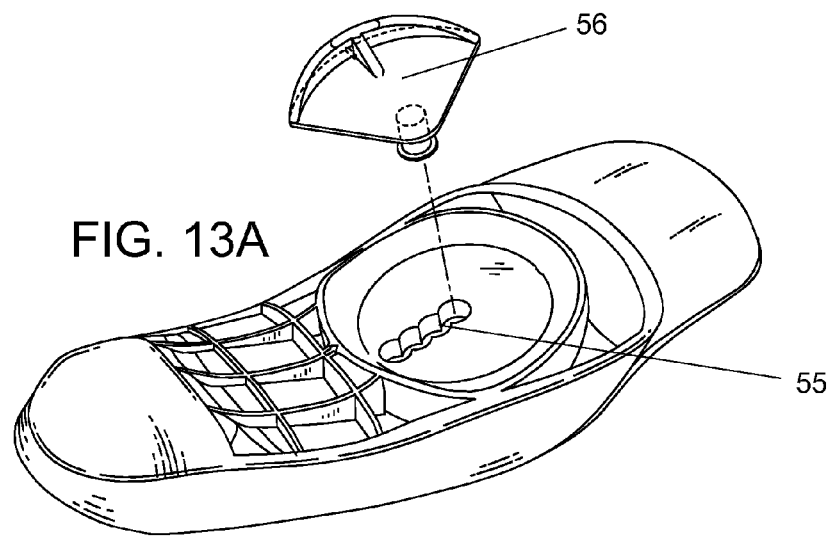
FIGS. 13A-13D are views of the fourth embodiment with retractable posting.
Figure 13B:
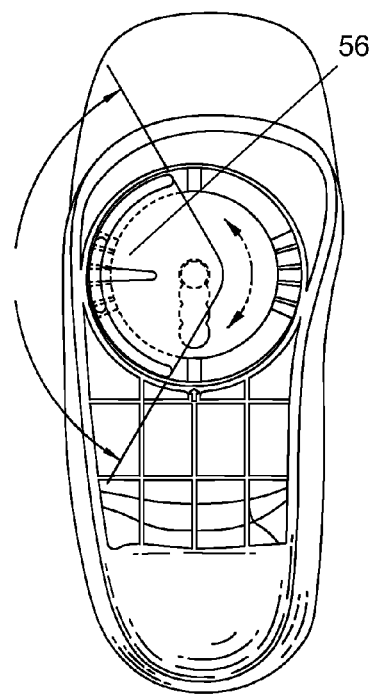
Figure 13C:
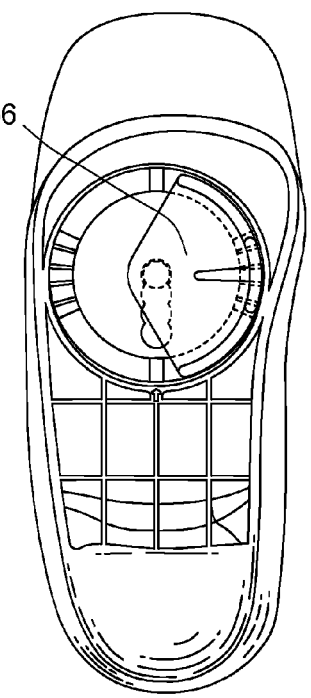
Figure 13D:
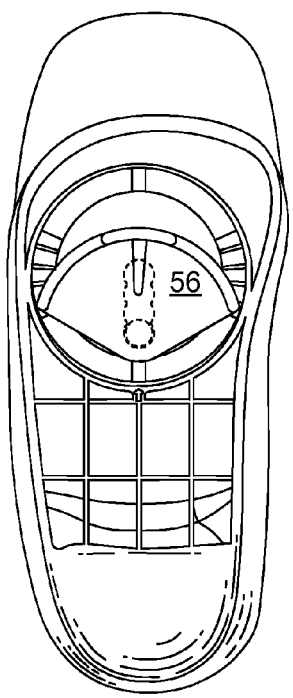

The third embodiment as seen in FIGS. 12A-12C has two separate symmetric tilt selectors 50L 50R. One is on the left 50L and one on the right 50R. They are each slideable along their respective arcuate slots 51L 51R. In this specific version, the lift plates' can be thought of as portions of a lift plate as in the initial embodiment. Their repositionability by sliding moves them through the identical positions as that of the counterpart in the initial embodiment with the circular selector.

Ring-Shaped Variation

A variation of this would be a circular lift plate rotationally constrained at its circumference by a slot structure rather than pivotally constrained at its center. Some versions, freed of needing a center connection, might consist primarily of an annular shaped circumferential configuration. This can have the benefit of reduced mass and structure.

Fourth Embodiment

The fourth embodiment seen in FIGS. 13A-D, has a lift or selector plate 56 similar to that of the second embodiment. However rather than only pivoting about a fixed center position, the selector is coupled to the orthotic plate by a slot 55. One extremity of the slot is the center position about which the selector can rotate in the same manner as that of the second embodiment. However, the slot allows the selector to be retracted towards the arch. This is an alternate configuration for moving a selector to a neutral position where no posting is presented. In some cases, this may allow a greater degree of flexing of the orthotic plate before a "bottoming out" of the tucked away selector occurs.

Fifth Embodiment

An apparatus similar to many of the above embodiments might also be integrated into a shoe or boot. In that case, illustrated in FIG. 14 a shoe 70 can have an opening 71 on its underside that allowed a user to make a pivoting adjustment to the lift plate. In that case, there would be no need to remove the orthotic plate from the item of footwear in order to make an adjustment.

Figure 16:
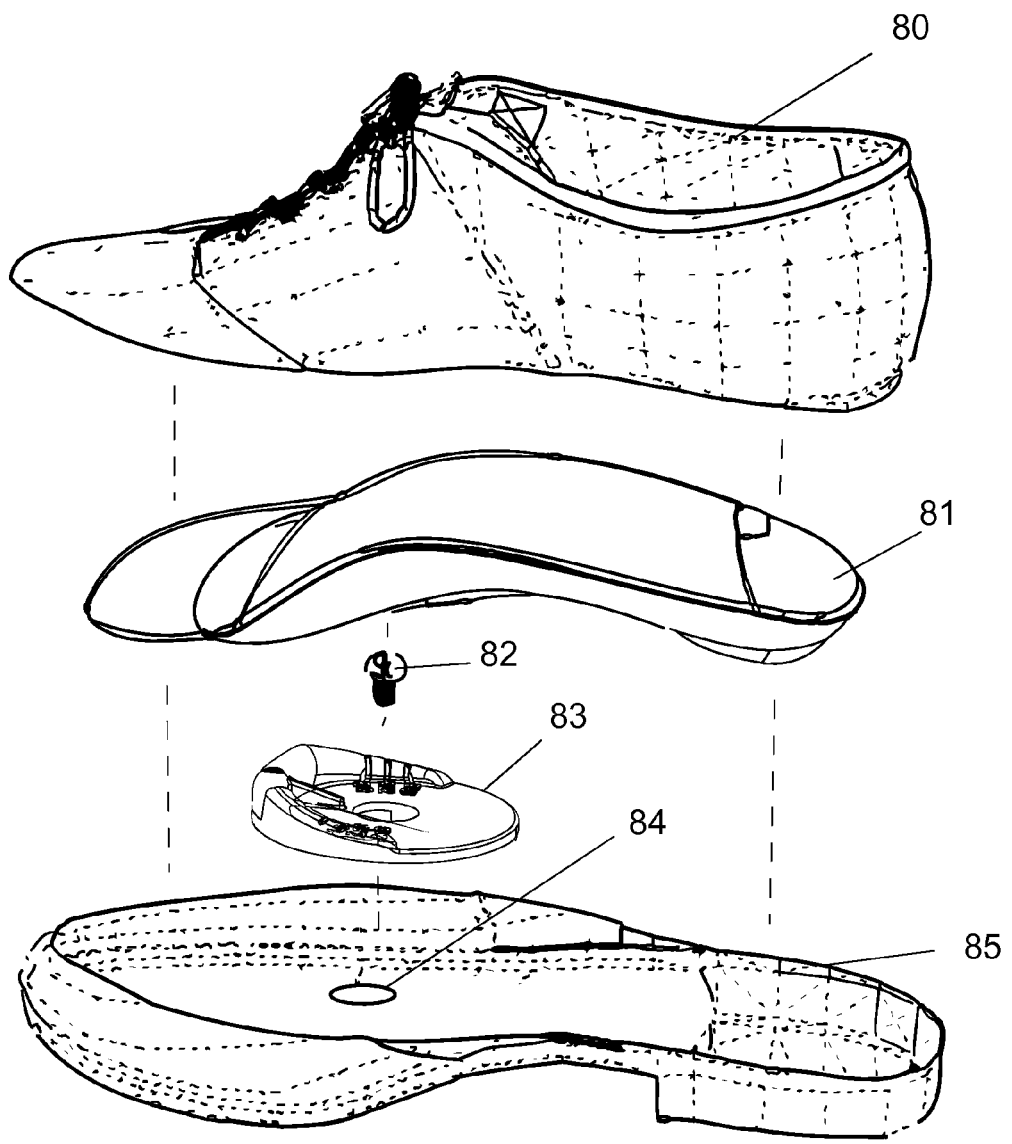
FIG. 16 is an exploded perspective view of an embodiment with the selector wheel upside down and secured to the inner sole of a shoe.

Another style of embodiment including footwear has a selector pivotally attached to the inside of a shoe or boot "upside down" rather than to the underside of a foot-receiving platform. In this case, the foot-receiving platform would rest on the floor of the shoe or boot including resting on a protrusion on the selector. This embodiment is illustrated in FIG. 16 in a perspective, exploded manner. A shoe is shown cut into an upper portion 80 and a lower portion 85. This is not intended to imply any construction technique but to allow a view into the inside of the shoe. The lower portion has an opening 84 for attachment of the selector wheel 83. In this case, the wheel is rotationally coupled to the inner sole of the shoe by a screw 82. The orthotic plate itself 81 rests upon the inner sole and upon a portion of the wheel's protrusions if the wheel is turned appropriately to cause a tilt.

The adjustability and variation on the forefoot angle would be comparable to other embodiments but with the selector not necessarily directly attached to the foot receiving plate. Adjustment could be by removal of the orthotic plate allowing access to the selector from the inside of the shoe. Alternatively, it could be adjusted externally as in the above shoe of FIG. 14.

Operation

Other Embodiments

The other shown embodiments have an analogous operation to that of the initial embodiment. In embodiment three, the individual selectors would normally be positioned so that either the left or the right selector was fully retracted while the other was in a desired forward position. As mentioned above the fourth embodiment allows for a slidable retraction of the selector plate to an out-of-the-way position.

Variations

Those skilled in the art will be aware of materials, techniques, and equipment suitable to produce the example embodiments presented as well as variations on the those examples. This teaching is presented for purposes of illustration and description but is not intended to be exhaustive or limiting to the forms disclosed. Many modifications and variations will be apparent to those of ordinary skill in the art. The embodiments and versions help to explain the principles of the invention, the practical application, and to enable others of ordinary skill in the art to understand it. Various embodiments with various modifications as are suited to the particular application contemplated are expected.

Materials and Alternatives

The described devices might be composed of material including polypropylene, polyurethane, polyethylene, and polystyrene. Thermoplastic elastomeric materials and synthetic rubbers including thermoplastic rubbers are also useable in this application. Various degrees of hardness may be appropriate for the foot receiving shell platform and other for the lift plate. Although the example described has been of a shoe or footwear insert, the posting system might be used on the exterior of a shoe or a shoe-sock as well. Footwear includes ice skates, roller skates, golf cleats, ski boots and other specialized foot coverings.

In some versions a lock pin or other structure might be provided to keep the lift plate in a particular position. The body or foot receiving surface in some versions can be custom molded and in other versions pre-made in various sizes and styles. A kit might include multiple bodies and multiple lift plates. Generally, embodiments obviate the need for grinding or add-on posts. Also, although illustrated and explained with one or two secured pivot-able lift plate, versions might have multiple lift plates or selectors that are independently pivotable or otherwise repositionable. Some versions might only provide tilt towards the outside and others might only provide tilt toward the inside. Others might provide a forward or a backward tilt.

Aspects of the Invention

A. In one aspect the invention comprises an item of footwear with a selector wheel rotatably and abuttally secured to the inside sole; the flat bottom side of the selector wheel is adjacent to the flat upper side of the inner sole; the selector wheel has regions of varying height at different angular locations on its upper facing surface; a foot receiving plate rests in the shoe being supported by the inside sole and by raised portions of the selector wheel; the shoe, selector wheel and foot receiving plate are so shaped and configured as to provide an adjustable tilt to a foot, the adjustment being by rotation or pivoting of the selector wheel.

B. The aspect of the invention of aspect A above where the adjustability is provided for at the underside of the footwear.

In the following claims, the words "a" and "an" should be taken to mean "at least one" in all cases, even if the wording "at least one" appears in one or more claims explicitly. Claims that speak of multiple degrees of tilt may have one of the multiple degrees of tilt as no significant added tilt at all. The scope of the invention is set out in the claims below.

It is claimed:

1. A foot support device comprising:
   a forefoot post comprising at least a thick region and a distinct thin region;
   a contoured, semi-rigid foot receiving plate;
   the post mechanically coupled abuttingly to the lower surface of the plate at a forefoot region of the plate, where the coupling provides a constrained, ready repositionability between post and plate providing for a first state and a second state of the device; the first state fixing the thick region in an operative position such that, in use, the dimensions of the thick region are determinative of the tilt of the plate and the thin region is in a non-operative position; the second state fixing the thin region in an operative position such that, in use, the dimensions of the thin region are determinative of the tilt of the plate and the thick region is in a non-operative position where the thick region does not support the plate.

2. The foot-supporting device of claim 1 where the coupling is a pivoting coupling.

3. The foot-supporting device of claim 1 where the coupling is a sliding coupling.

4. The foot-supporting device of claim 1 where the coupling is a rotating coupling.

5. The foot-support device of claim 1 where the range of repositionability and the configuration of the plate and post are such that an operative position is proximate to the medial edge of the foot receiving plate.

6. The foot-support device of claim 1 where the constraints of repositionability and the configuration of the plate and post are such that an operative position is proximate to the lateral edge of the foot receiving plate.

7. The foot-supporting device of claim 1 where the range of repositionability and the configuration of the plate and post are such that a first operative position is proximate to the medial edge of the foot receiving plate and a second operative position is proximate to the lateral edge of the plate.

8. A method of adjusting a forefoot post using the foot support device of claim 1 where the post is a selector method comprising:

a) walking with that device between a foot and a supporting surface with the selector set to a first state;
   after the degree of tilt has been adjusted by pivoting the selector of the device to a second state; and,
   b) walking with the device set in the second state.

9. The device of claim 1 where a non-operative region is located under a raised region of the foot receiving plate and provides no supportive contact with the horizontal plane immediately beneath the device.

10. The foot support device of claim 1 where the post further comprises a region of intermediate thickness and the coupling's repositionability provides a third state where the dimensions of the intermediate region are determinative of the tilt of the plate and the thick region is in a non-operative position below a raised area of the foot receiving plate.

11. A device having a tilt selector readily mechanically coupleable to the underside of a semi-rigid foot receiving plate in an abutted manner, the coupling being a pivotal connection and the selector having at least one raised region relative to other distinct regions and the device configured such that pivoting the selector relative to the plate from a neutral orientation state to a first state selectively locates the at least one raised region where the relative height of that region is solely determinative of the change in overall tilt of the foot receiving plate between the neutral orientation state and the first state, when in use.

12. The device of claim 11 where the at least one raised region is at least two raised regions and in a second state of orientation, reached by pivoting, a second raised region's height is solely determinative of the change in overall tilt between the neutral state and the second state.

13. An adjustable orthotic device comprising:
   a) a semi-rigid plate of a thin construction having an upper surface of a shape adapted for receiving a foot and an opposing lower surface with a raised portion;
   b) a selector having an upper surface and an opposed lower surface, the thickness between the surfaces differing between at least two respective portions of the selector;
   the selector rotatably coupled to the plate with the upper surface of the selector adjacent to the lower surface of the plate; further, the lowermost portions of the plate and of the selector collectively defining a plane; rotation of the selector bringing alternate distinct thickness portions into position as the lowermost portion of the selector and removing selector portions of other thicknesses from defining the plane.

14. The device of claim 13 where some portions of differing thickness, collectively comprises a sloped shape.

15. The device of claim 13 where the selector has a circular shape.

16. The device of claim 13 where the selector has an annular shape.

17. The device of claim 1 where a heel region of the foot receiving plate is hollow and closed on the top surface of the foot receiving plate and open on its bottom surface.

18. The device of claim 17 where the distance from the top surface of foot receiving plate to the upper extent of hollow region is about 0.125 inches.

19. An item of footwear in combination with posting system of claim 13.

20. The combination of claim 19 where the footwear is a shoe.

21. The combination of claim 20 where the selector can be selectively repositioned via the outside of the sole of the shoe.

22. The combination of claim 19 where the footwear is a sock.

23. The footwear of claim 19 where the footwear is a boot.

24. A foot support system comprising:
a forefoot post comprising at least a thick region and a thin region;
a contoured, semi-rigid foot receiving plate;
a base;
the post mechanically coupled abuttingly to the upper surface of the base, where the coupling provides a constrained, ready repositionability between post and base providing, in use, for a first state and a second state of the system; the first state fixing the thick region in an operative position with the thin region in a non-operative position; and the second state fixing the thin region in an operative position and the thick region in a non-operative position; and where the in use configuration is the base resting parallel to the ground with the foot receiving plate resting on the base with a forefoot region of the plate supported by the operative portion of the post and non-operative portions of the post not supporting the plate.

25. The foot support system of claim 24 where the coupling is a rotating coupling.

26. The foot support system of claim 24 where the operative position is proximate to the medial edge of the base.

27. The foot support system of claim 24 where the base is a component of an article of footwear.

* * * * *